US010327667B2

(12) United States Patent
Sonderegger (10) Patent No.: US 10,327,667 B2
(45) Date of Patent: Jun. 25, 2019

(54) ELECTRO-MAGNETIC NEEDLE CATHETER INSERTION SYSTEM

(71) Applicant: Becton, Dickinson and Company, Franklin Lakes, NJ (US)

(72) Inventor: Ralph L. Sonderegger, Farmington, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 409 days.

(21) Appl. No.: 15/154,362

(22) Filed: May 13, 2016

(65) Prior Publication Data

US 2017/0325714 A1 Nov. 16, 2017

(51) Int. Cl.
| A61B 5/06 | (2006.01) |
| A61B 5/00 | (2006.01) |
| A61M 5/32 | (2006.01) |
| A61M 25/01 | (2006.01) |
| A61M 25/06 | (2006.01) |
| A61B 8/08 | (2006.01) |
| A61B 17/34 | (2006.01) |
| A61B 34/20 | (2016.01) |

(52) U.S. Cl.
CPC ............ *A61B 5/062* (2013.01); *A61B 5/0035* (2013.01); *A61B 8/0841* (2013.01); *A61M 5/32* (2013.01); *A61M 25/0102* (2013.01); *A61M 25/0108* (2013.01); *A61M 25/0127* (2013.01); *A61M 25/0606* (2013.01); *A61M 25/0693* (2013.01); *A61B 2017/3413* (2013.01); *A61B 2034/2051* (2016.02); *A61M 2205/8206* (2013.01)

(58) Field of Classification Search
CPC ..... A61B 5/062; A61B 5/0035; A61B 8/0841; A61B 2017/3413; A61B 2034/2051; A61M 5/32; A61M 25/0102; A61M 25/0108; A61M 25/0127; A61M 25/0693; A61M 25/0606; A61M 2205/8206
USPC ................................................ 600/407-480
See application file for complete search history.

(56) References Cited

U.S. PATENT DOCUMENTS

| 6,337,627 B1* | 1/2002 | Von Gutfeld ............ A61B 5/06 324/207.12 |
| 6,537,232 B1* | 3/2003 | Kucharczyk ............ A61B 5/031 600/411 |
| 2002/0052546 A1* | 5/2002 | Frantz ...................... A61B 5/06 600/424 |

(Continued)

OTHER PUBLICATIONS

PCT International Search Report and Written Opinion dated Aug. 28, 2017, 17 pgs.

*Primary Examiner* — Sanjay Cattungal
(74) *Attorney, Agent, or Firm* — Servilla Whitney LLC (57) ABSTRACT

A device for magnetizing a tissue-penetrating medical device is disclosed including a housing having a proximal portion and a distal portion; a magnetic field generator contained within the distal portion of the housing and a tissue penetrating subassembly including a hub and a tissue penetrating medical device having a proximal end and a distal end. The hub is detachably connected to the distal portion of the housing and the proximal end of tissue penetrating medical device extends proximally from the hub such that the proximal end of the tissue penetrating medical device is exposed to the magnetic field to magnetize the distal end of the tissue penetrating medical device. Methods of magnetizing tissue-penetrating medical devices are also disclosed.

29 Claims, 3 Drawing Sheets

(56) References Cited

U.S. PATENT DOCUMENTS

| | | | |
|---|---|---|---|
| 2008/0132911 A1* | 6/2008 | Sobe | A61B 10/0233 |
| | | | 606/130 |
| 2008/0237367 A1* | 10/2008 | McNichols | F02M 27/08 |
| | | | 239/102.2 |
| 2013/0263668 A1* | 10/2013 | Hyun | G01H 1/00 |
| | | | 73/647 |
| 2014/0046261 A1* | 2/2014 | Newman | A61M 25/0127 |
| | | | 604/158 |
| 2014/0257080 A1* | 9/2014 | Dunbar | A61B 8/4416 |
| | | | 600/409 |
| 2014/0296694 A1* | 10/2014 | Jaworski | A61B 8/463 |
| | | | 600/409 |
| 2017/0325714 A1* | 11/2017 | Sonderegger | A61B 5/0035 |

* cited by examiner

ELECTRO-MAGNETIC NEEDLE CATHETER INSERTION SYSTEM

FIELD

Aspects of the present disclosure relate to a device for magnetizing a tissue-penetrating medical device.

BACKGROUND

Emerging medical procedural guidance systems utilize a combination of ultrasound and magnetic technologies to visualize a patient's sub-dermal anatomy and to provide guidance for positioning an invasive medical device, for example, a needle, a stylet or a guidewire. The combination of ultrasound and magnetic methods allows for estimation of the position of the insertion device relative to the patient's anatomy, and thereby improves the likelihood of successfully accessing the vascular and completing the invasive procedure.

Ultrasound and magnetic procedural guidance system technology relies on the invasive device having a magnetic field source. One way to magnetize a portion of the invasive device prior to insertion is by using an externally applied magnetic field. For systems that apply an external magnetic field, the portion of the invasive device that is targeted for magnetization is the metal cannula of the invasive device, for example, the cannula of a needle. For this type of system, a separate device with integrated magnets is used to actively magnetize the needle just prior to the insertion procedure.

Systems that require the user to actively magnetize the metal cannula have certain limitations and inherent risks as this approach does not guarantee consistent magnetization given the reliance of the user to place the needle into the needle magnetizer and the variation of how this is done (i.e. depth, speed, centering, etc.).

Thus, there is a need for a system that passively and consistently magnetizes the needle while reducing or eliminating risks, such as needle tip damage and needle contamination.

SUMMARY

A first aspect of the disclosure pertains to a device for magnetizing a tissue-penetrating medical device. A first embodiment pertains to a device comprising a housing having a proximal portion and a distal portion, and a magnetic field generator contained within the distal portion of the housing to produce a magnetic field, and a tissue penetrating subassembly. In one or more embodiments, the device further comprises a power supply in electrical communication with the magnetic field generator, a switch in communication with the power supply to activate and deactivate the magnetic field generator. In one or more embodiments, the device utilizes a permanent magnet, and in such embodiments, a power supply may not be required In one or more embodiments, the tissue penetrating subassembly includes a hub and a tissue penetrating medical device having a proximal end and a distal end. The hub is detachably connected to the distal portion of the housing and the proximal end of tissue penetrating medical device extends proximally from the hub such that the proximal end of the tissue penetrating medical device is exposed to the magnetic field and the distal end of the tissue penetrating medical device is magnetized upon exposure of the proximal end of the tissue penetrating medical device by the magnetic field. In one or more embodiments, the hub is detachably connected to the distal portion of the housing by a latch assembly.

In one or more embodiments, the housing further includes a controller in communication with the power supply and the magnetic field generator. The controller controls the magnitude of the magnetic field generated by the magnetic field generator. The magnetic field generated may be constant or variable, and the controller can control magnitude and variance of the magnetic field.

In one or more embodiments, the tissue-penetrating medical device may be a needle or stylet. In a specific embodiment, wherein the tissue penetrating medical device is a needle, the needle when magnetized can be used with a procedural guidance system including an ultrasound system which can be used to locate and project the position of the magnetized needle during an invasive medical procedure.

In one or more embodiments, the power supply is a direct current power supply, which may comprise a single battery or a plurality of batteries. In yet another embodiment, the power supply is an alternating current power supply.

In one or more embodiments, a flash chamber may be located within the hub of the tissue penetrating medical device. The flash chamber may include a vent plug which seals upon flow of blood into the flashback chamber.

In one or more embodiments, the distal end of the tissue penetrating device includes a notch to provide immediate confirmation of vessel entry at a point of insertion.

A second aspect of the disclosure pertains to a device for magnetizing a tissue-penetrating medical device having a catheter. In one or more embodiments, a device comprises a housing having a proximal portion and a distal portion, a magnetic field generator contained within the distal portion of the housing, a tissue penetrating subassembly including a catheter having a proximal end and a distal end, an introducer needle extending through the catheter, a catheter adapter having a distal end and a proximal end, an internal cavity, and a tip region having a distal opening having a circumference through which the catheter extends. In one or more embodiments, the catheter adapter is connected to the proximal end of the catheter. In one or more embodiments, a needle hub is connected to the proximal end of the introducer needle, the hub detachably connected to the distal portion of the housing. The proximal end of introducer needle extends proximally from the hub such that the proximal end of the introducer needle is exposed to the magnetic field and the distal end of the introducer needle is magnetized upon exposure of the proximal end of the introducer needle by the magnetic field. In one or more embodiments, the device further comprises a power supply in electrical communication with the magnetic field generator, a switch in communication with the power supply to activate and deactivate the magnetic field generator. In one or more embodiments, the device utilizes a permanent magnet, and in such embodiments, a power supply may not be required.

In one or more embodiments, the needle hub is detachably connected to the distal portion of the housing by a latch.

In one or more embodiments, a flash chamber may be located within the needle hub of the introducer needle. The flash chamber may include a vent plug which seals upon flow of blood into the flashback chamber.

In one or more embodiments, the introducer needle includes a notch to provide immediate confirmation of vessel entry at a point of insertion.

A fourth aspect of the disclosure pertains to a method for magnetizing a tissue-penetrating medical device comprising obtaining a tissue penetrating medical device having an elongated needle having a proximal end and a distal end. The elongated needle is disposed in a needle hub subassembly such that the proximal end of the elongated needle extends in a proximal direction from the hub and the distal end of the elongated needle extends in a distal direction from the hub towards a patient. The method includes obtaining a housing having a proximal portion and a distal portion wherein the housing includes a magnetic field generator contained within the distal portion of the housing. A power supply is in electrical communication with the magnetic field generator, and a switch is in communication with the power supply to activate and deactivate the magnetic field generator. The method further includes connecting the needle hub assembly to a distal portion of the housing such that the proximal end of the elongated needle is exposed to the magnetic field generator and depressing the switch in communication with a power supply to activate a magnetic field generator to magnetize the elongated needle. The method further includes positioning the distal end of the elongated needle adjacent to a desired point of vascular entry and inserting the magnetized elongated needle into a patient's vasculature. In one or more embodiments, the method further includes using an ultrasound imaging device to visualize the magnetized elongated needle.

DETAILED DESCRIPTION

Before describing several exemplary embodiments of the disclosure, it is to be understood that the description provided is not limited to the details of construction or process steps set forth in the following description. The devices described herein are capable of other embodiments and of being practiced or being carried out in various ways.

In this disclosure, a convention is followed wherein the distal end of the device is the end closest to a patient and the proximal end of the device is the end away from the patient and closest to a practitioner.

Aspects of the disclosure pertain to a device for magnetizing a tissue-penetrating medical device and for generating a magnetic field for a tissue penetrating medical device, such as a needle, in order to improve visualization during insertion into a vein using ultrasound imaging. One or more embodiments relate to a device comprising a disposable tissue penetrating medical device detachably connected to a reusable magnetic field generator contained within a distal portion of a housing to produce a magnetic field. According to one or more embodiments, the magnetic field generator can be reused numerous times to magnetize an unlimited number of tissue penetrating medical devices. While specific embodiments show an introducer needle used in combination with a catheter such as a peripheral intravenous catheter, it is understood that that devices described in this disclosure can be used on a variety of tissue-penetrating medical devices, including, but not limited to stylets, guidewires, spinal needles, epidural needles, hypodermic needles and introducer needles used with catheters. In one or more specific embodiments, the tissue-penetrating medical devices comprise a needle with a hollow cannula, which can be used to remove fluids from a patient or deliver fluids to a patient. According to one or more embodiments, systems and devices are provided which can passively and consistently magnetize tissue-penetrating medical devices. According to one or more embodiments, passive magnetization of tissue-penetrating medical devices can be accomplished without any additional or new clinical steps, a more consistent and predictable magnetic field can be provided. In one or more embodiments, magnetization can be accomplished with no additional risk of damage to the tissue-penetrating medical device, and the device and system does not introduce additional risk for contamination of the tissue-penetrating medical device.

Figures 1, 3:
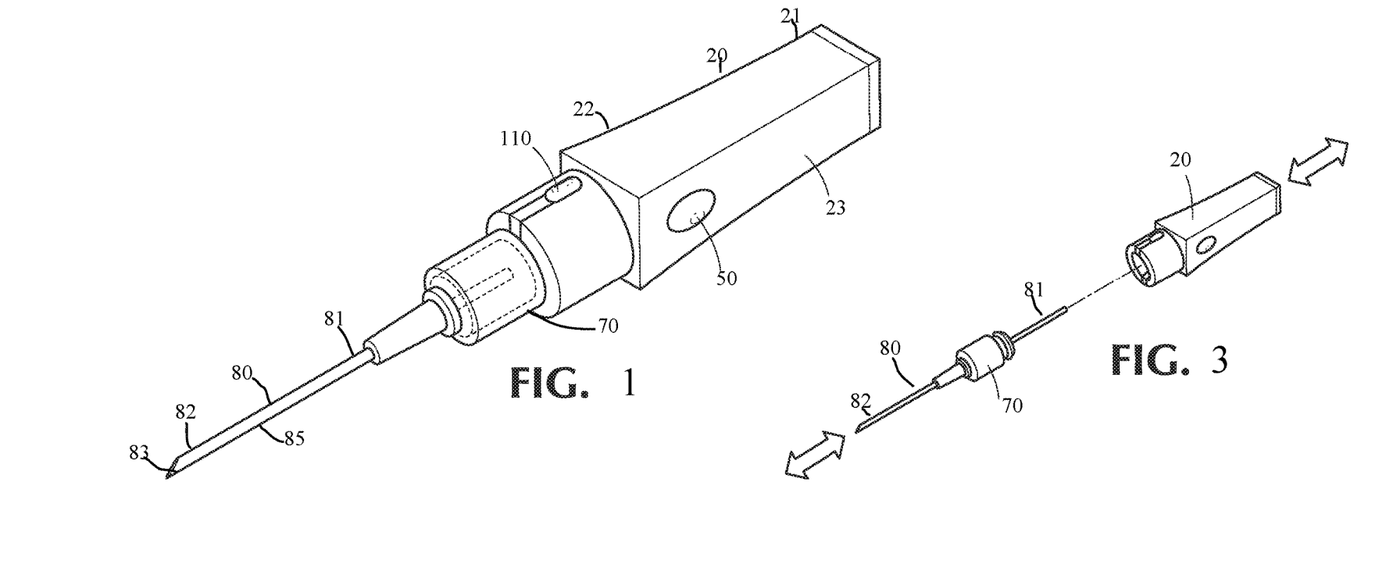
FIG. 1 shows a perspective view of an embodiment of a device for magnetizing a tissue-penetrating medical device of the present disclosure.
FIG. 3 shows a perspective view of an embodiment of a device for magnetizing a tissue-penetrating medical device of the present disclosure wherein the housing is separated from the tissue penetrating subassembly.

Referring now to FIG. 1, one aspect of the disclosure pertains to pertains to a device 10 comprising a housing 20 having a proximal portion 21 and a distal portion 22, a magnetic field generator 30 contained within the distal portion 22 of the housing 20 to produce a magnetic field, a power supply 40 in electrical communication with the magnetic field generator 30; a power switch 50 in communication with the power supply 40 to activate and deactivate the magnetic field generator 30; and a tissue penetrating subassembly 60.

The tissue penetrating subassembly 60 includes a hub 70 and a tissue penetrating medical device 80 having a proximal end 81 and a distal end 82. The hub 70 may be detachably connected to the distal portion of the housing 20. The proximal end 81 of the tissue penetrating medical device 80 extends proximally from the hub 70 such that the proximal end 81 of the tissue penetrating medical device is exposed to the magnetic field and the distal end 82 of the tissue penetrating medical device is magnetized upon exposure of the proximal end 81 of the tissue penetrating medical device 80 by the magnetic field.

In one or more embodiments, the magnetic field generator 30 further includes a coil 31 that is electrically energized by the magnetic field generator 30 to produce a magnetic field in and around the tissue penetrating medical device 80.

Housing 20 includes a grip 23 and encloses a coil 31 of the magnetic field generator 30, controller 90, power supply 40 and latch assembly 110. Grip 23 is the portion of the housing 20 that the clinician would typically hold during insertion of the tissue penetrating medical device 80 into a patient. In one or more embodiments, housing 20 is removably connected to a tissue penetrating medical device 80. In one or more embodiments, the tissue penetrating medical device 80 is disposable.

Housing 20 further includes a power switch 50 which is in communication with the power supply 40 to activate and deactivate the magnetic field generator 30 that induces the flow of current to the coil 31 from the power supply 40 to magnetize the tissue penetrating medical device 80. The ability to selectively activate the flow of current from the power supply 40 to the coil 31 during active use allows for the preservation of the power supply 40.

In one or more embodiments, the power supply 40 comprises a direct current power supply, which may include one or more batteries 102. In yet another embodiment of the present disclosure, power switch 50 may be in the form of a side-push power button located on the side of device 10, potentially molded into the side of the housing 20 as shown in FIG. 1. Alternatively, power switch 50 may be in the form of a top or top-mounted button (not shown) into the housing 20 or grip 23 of device 10, the device can be activated by pressing power button to magnetize the tissue penetrating medical device 80. The power switch 50 can be configured in a variety of ways, such as a rocker switch, a sliding switch, a toggle switch, or a rotary switch. After activating the device 10 by contacting the power switch 50 to magnetize the needle, the needle can be inserted into a skin surface of a patient. In one or more embodiments, the tissue penetrating medical device 80 may be a needle and/or catheter, wherein the needle and catheter can be inserted into a skin surface after activating the device by depressing the power switch 50 to magnetize the needle.

The power supply 40 may be in the range of 5 to 20 volts. Power supply 40 may comprise any suitable device that is capable of supplying power to controller 90, magnetic field generator 30 and coil 31 to fulfill its intended purpose. Some examples of suitable DC power supply include one or more batteries 102 or a capacitor. Batteries 102 may include a low-cost, commercially-available button-cell, hearing-aid, or watch type battery. In one or more embodiments, power supply 40 is a DC battery or capacitor that is contained within housing 20. By way of illustration, FIG. 1 shows one embodiment in which the power supply 40 comprises one or more batteries 102 to supply power to the controller 90, magnetic field generator 30 and coil 31. Controller 90 may include one or more printed circuit boards 91. In one or more embodiments, the proximal portion 21 of the housing 20 includes a battery access lid 103 to allow access to batteries 102.

In yet another embodiment, the power supply comprises an alternating current ("AC") power supply. An example of a suitable AC power supply is a suitable connection (e.g., a plug, transformer, and/or another suitable component) to a power grid, such as a municipal power supply. In one or more embodiments, the power supply is a power cord (not shown) attached to the proximal portion of the housing.

As shown in FIG. 1, the device comprises one or more electrical components, including wiring, which are configured to electrically connect the power supply 400, controller 90 and coil 31. In one or more embodiments, controller 90 can include one or more printed circuit boards.

In one or more embodiments, the tissue penetrating subassembly 60 includes a hub 70 and a tissue penetrating medical device 80 having a proximal end 81 and a distal end 82. Hub 70 is detachably connected to the distal portion 22 of the housing 20 and the proximal end 81 of tissue penetrating medical device 80 extends proximally from the hub 70 such that the proximal end 81 of the tissue penetrating medical device is exposed to the magnetic field and the distal end 82 of the tissue penetrating medical device 80 is magnetized upon exposure of the proximal end 81 of the tissue penetrating medical device 80 by the magnetic field.

In one or more embodiments, the tissue penetrating medical device 80 may be a needle. Herein the term "needle" will include standard needles, such as hypodermic needles, spinal needles, epidural needles, introducer needles used with catheters and other like devices that may be used to access an anatomical structure near the outer surface of a body and/or deliver a fluid thereto. In one or more embodiments, the needle has a hollow cannula that can withdraw fluids from or deliver fluids to a patient.

In a specific embodiment, the tissue penetrating medical device 80 may be in form of a needle. The needle when magnetized can be used with a procedural guidance system including an ultrasound detector which can locate and project the position of the needle during an invasive medical procedure. In one or more embodiments, the tissue penetrating device may be needle with a hollow cannula. The needle with the hollow cannula can comprise virtually any rigid tube that includes a sharpened distal tip and which is configured to puncture a patient's body, to access an intended space, and to withdraw or to introduce a material (e.g., a fluid) from or into the intended space. A suitable cannula may include an introducer needle for use in an IV catheter assembly (e.g., an over-the-needle peripheral IV catheter assembly), a venous needle, and an arterial needle.

The tissue penetrating medical device 80 is made of a magnetizable metallic material. In one or more embodiments, the magnetizable metallic material may be stainless steel or similar materials.

In one or more embodiments, the tissue penetrating medical device 80 includes a solid body that extends from the distal end 82 to the proximal end 81. In one or more embodiments, the tissue penetrating medical device 80 further includes an interior lumen that extends through the tissue penetrating medical device 80 from the distal end 82 to the proximal end 81. Tissue penetrating medical device 80 may include a beveled tip 83 formed in the distal end of the tissue penetrating medical device 80 to facilitate entry into a body. In some embodiments, coil 31 extends only over the proximal end of the tissue penetrating medical device 80. Alternatively, in some embodiments, coil 31 extends over the entire shaft of tissue penetrating medical device 80 excluding only a beveled tip 83 at the distal end 82.

When magnetized, tissue penetrating medical device 80 can be used with a procedural guidance system including one or more ultrasound detectors to locate and project the position of the needle during an invasive medical procedure.

Figure 2:
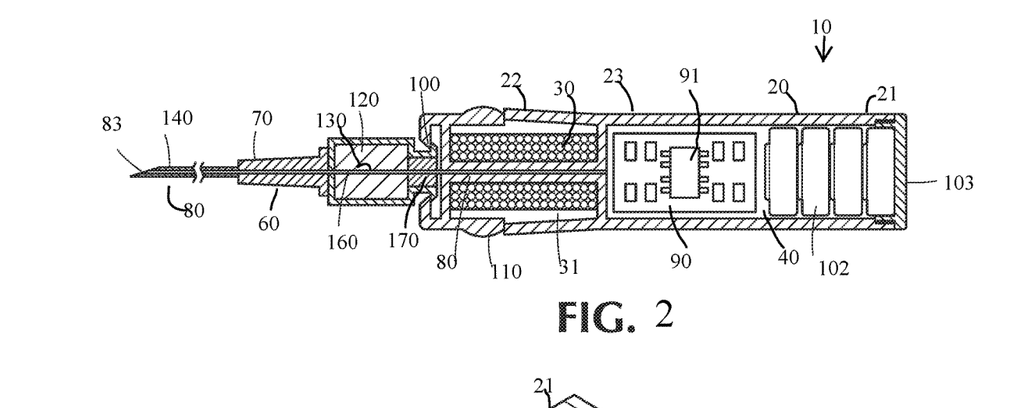
FIG. 2 shows a cross-sectional view of an embodiment of a device for magnetizing a tissue-penetrating medical device of the present disclosure.

In one or more embodiments, as shown in FIGS. 2 and 3, the tissue penetrating medical device 80 may be a needle that extends both in the distal and proximal direction from hub 70 of the tissue penetrating medical device 80. The elongated needle must be long enough to be enveloped within the coil, which, when energized, will generate a magnetic field surrounding the needle, thus magnetizing the needle. In the embodiment shown in FIG. 3, the tissue penetrating medical device 80 may be discarded after a single use. In contrast, the housing 20 may be reused many times with many different needles. Additionally, because the housing 20 is not discarded after a single use, the housing 20 may comprise more expensive components, including one or more printed circuit boards, magnetic field generator and power supply.

In one or more embodiments, a latch 100 mechanically connects the hub 70 to the distal portion 22 of the housing 20 and the proximal end 81 of tissue penetrating medical device 80. As shown in FIG. 2, tissue penetrating medical device 80 may be in the form of an elongated needle extends proximally from the hub to fully penetrate coil 31.

In one or more embodiments, latch button 110 is a means of disengaging the latch 100 in order to remove the tissue penetrating medical device from the housing. The latch button 110, when pressed, actuates a latch 100 allowing the hub 70 of the tissue penetrating medical device 80 to be released from a hub retention element of the housing. In one or more embodiments, the latch 100 can be configured to secure the tissue penetrating subassembly 60 to the housing 20, such that pressing the latch button 110 permits removal of the tissue penetrating medical device 80 from housing 20. In one or more embodiments, latch button 110 can engage one or more detents on the housing such that the tissue penetrating medical device 80 cannot be removed from the housing 20 if the latch button 110 is in a first position, and can be removed when the latch button is in a second position. FIG. 2 illustrates a latch 100 engaging a slot in the base of the hub 70 to prevent inadvertent separation of the tissue penetrating subassembly 60 from the housing 20. In one or more embodiments, the latch button 110 may be included on housing 20. In one or more embodiments, the latch button may include alignment pins to engage the needle hub. In one or more embodiments, the latch button is configured to be pushed downward into the device, and comprises guide slots for engaging and releasing the needle hub.

In one or more embodiments, as shown in FIG. 2, latch 100 may be mushroom-shaped and includes a cap portion and a stem portion. When the latch 100 is slotted between the cap and the base adjacent the stem portion, the housing is latched onto the base, as illustrated in FIG. 2. Latch 100 may frictionally engage one or more of the cap portion, stem portion and a portion of the base adjacent to the stem portion, in the latched state, as illustrated in FIG. 2.

Thereafter, when a user wishes to remove the tissue penetrating medical device 80 from the base that holds the tissue penetrating medical device, the user presses the latch button 110 so that the latch 100 becomes disengaged from the housing 20 allowing the tissue penetrating medical device 80 to be separated from the housing 20.

In one or more embodiments, latch 100 may include a pair of levers, each having an arm. The levers are hinged to housing and the levers can be biased by depressing the latch button 110. In order to connect the hub to the housing, the user aligns the hub to a corresponding slot in the housing and engages the arms of the levers by releases the latch button to lock the arms of the levers into the pockets and catches of the housing. In order to disconnect the hub 70 from the housing 20, the user squeezes or depresses the latch button to release the levers of the hub from the pockets and catches of the housing. Thereafter, the user can lift the hub from the housing to separate the hub 70 from the housing 20.

In one or more embodiments, the power switch 50 and latch button 110 may have finger bumps to aid the user in locating and using the respective buttons.

In one or more embodiments, the housing 20 further includes a controller 90 in communication with the power supply 40 and the magnetic field generator 30 which controls the magnitude of the magnetic field generated by the magnetic field generator 30. The magnetic field generated may be constant or variable. In one or more embodiments, the controller 90 may include a printed circuit assembly that supplies and regulates power to the coil 31 and generates a magnetic field around the tissue penetrating medical device 80. In one or more embodiments, controller 90 may also allow for additional functions, such as Bluetooth communication with other devices, lighting, and any additional electronic features that may be desired during operation of the device.

Magnetic field generator 30 is capable of producing a constant or variable electromagnetic field as desired to allow for the creation of an easily differentiable magnetic signature to improve detection of the tissue penetrating medical device 80 at a receiving image device (not shown). Device 10 has the potential of producing an enhanced magnetic signature by modifying the intensity and/or frequency of the magnetic field.

A magnetic signature may take the form of binary informational pulses that could be interpreted by a receiving imaging device. Once recognized, the image may be enhanced and the signal amplified in relation to the background fields, to create a clearer image of the needle tip. In one or more embodiments, the magnetic field generator has the potential to produce a magnetic field on demand.

In one or more embodiments, a flash chamber 120 may be located within the hub 70 and is in fluid communication with the tissue penetrating medical device 80 to allow blood to flow into the flash chamber to provide the user with confirmation of vasculature entry. The flash chamber 120 may include a vent plug 130 which seals upon flow of blood into the flashback chamber.

In one or more embodiments, a number of safety features can be provided to prevent needle stick injuries. In one or more embodiments, the device may further comprise safety devices such as a needle shield and a needle sheath which covers the needle (not shown).

In one or more embodiments, the needle assembly may also include a shield engaged with a portion of the housing. The shield is movable over the tissue penetrating device from a retracted position in which the distal end is exposed, to an extended position in which the distal end is shielded by at least a portion of the shield. At least a portion of the flash chamber is visible in the retracted position.

The shield may at least partially surround the distal end of the tissue penetrating device in the extended position. Optionally, the shield is substantially circumferentially disposed about at least a portion of the cannula, and transition of the shield from the retracted position to the extended position telescopes the shield over the cannula. In certain embodiments, the sidewall of the cannula defines an opening extending between the cannula interior and the flash chamber.

In one or more embodiments, as shown in FIGS. 1 and 2, the flash chamber 120 may be integrally formed within a portion of the hub 70 of the tissue penetrating medical device 80. A porous vent may be disposed within the flash chamber such that the porous vent separates the flash chamber into a first chamber and a second chamber. The first chamber and the second chamber may be configured such that upon insertion of the distal end of the cannula into a patient, blood flows through the cannula and into the first chamber without sealing the porous vent. The flash chamber may include a vent mechanism in communication with an environment surrounding the needle assembly. The porous vent may include a plurality of pores for passage of blood from the first chamber to the second chamber. The vent mechanism may be a porous plug formed of a hydrophobic material, a one-way valve, or a porous plug formed of a hydrophilic material that swells on contact with blood.

In addition to flash chambers which may include a vent mechanism in communication with an external environment surrounding the needle assembly, it is also contemplated herein that a needle assembly may include a flash chamber having a vent plug which seals upon flow of blood into the flashback chamber, thereby inhibiting any pressurized air that may build up within the chamber, from moving in a reverse direction toward the inlet of the cannula.

In one or more embodiments, vent plug 130 allows air to escape from the flash chamber as it fills with blood. Once wetted, vent plug 130 becomes plugged as a result of exposure to blood.

In one or more embodiments, the distal end of the tissue penetrating medical device 80 includes a notch 140 to provide immediate confirmation of vessel entry at a point of insertion.

In one or more embodiments, the housing, hub, latch mechanism and safety device elements can be constructed of molded plastic materials, polycarbonate, thermoplastic polymers such as polyethylene terephthalate (PET and PETG), or similar materials.

Figures 4, 5, 6:
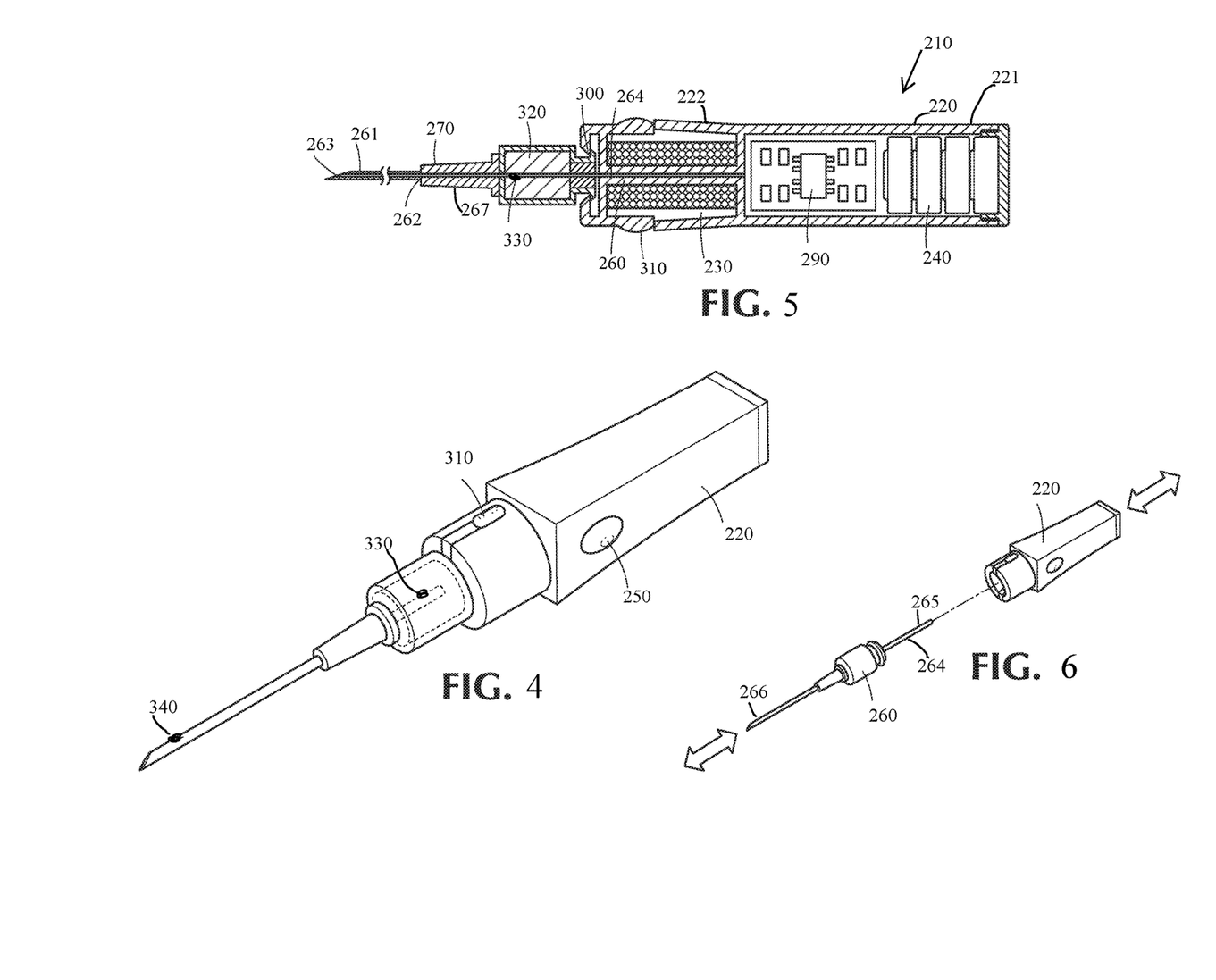
FIG. 4 shows a perspective view of another embodiment of a device for magnetizing a tissue-penetrating medical device of the present disclosure including a catheter assembly.
FIG. 5 shows a cross-sectional view of the embodiment as shown in FIG. 4 for magnetizing a tissue-penetrating medical device of the present disclosure.
FIG. 6 shows a perspective view of an embodiment of a device as shown in FIG. 4 wherein the housing is separated from the tissue penetrating subassembly.

A second aspect of the disclosure pertains to a device for magnetizing a tissue-penetrating medical device having a catheter. As shown in FIG. 4, in one or more embodiments, device 210 comprises a housing 220 having a proximal end 221 and a distal end 222, a magnetic field generator 230 contained within the distal end 222 of housing 220, a power supply 240 in electrical communication with the magnetic field generator 230, a switch 250 in communication with the power supply 240 to activate and deactivate the magnetic field generator 230, a tissue penetrating subassembly 260 including a catheter 261 having a proximal end 262 and a distal end 263, an introducer needle 264 having a proximal end 265 and distal end 266 extending through the catheter 261, a catheter adapter 267, an internal cavity 268, and a tip region 269 having a distal opening having a circumference through which the catheter extends, the catheter adapter 267 being connected to the proximal end 262 of the catheter, a hub 270 connected to the proximal end 265 of the introducer needle 264, the hub 270 detachably connected to the distal end 222 of the housing 220. The proximal end 265 of introducer needle 264 extends proximally from the hub 270 such that the proximal end 265 of the introducer needle is exposed to the magnetic field and the distal end 266 of the introducer needle is magnetized upon exposure of the proximal end 265 of the introducer needle 264 by the magnetic field.

The introducer needle 264 may have any component that is suitable for use with an IV catheter assembly. The introducer needle 264 is disposed within an internal cavity 268 of the catheter. The distal tip of the tissue penetrating device may comprise a standard bevel, a short bevel, a true short bevel, a bias grind point, a vet point, a lancet point, a deflected point (anti-coring), or another suitable known or novel needle point. The tissue penetrating medical device 80 may be any suitable length or any suitable gauge that allows it to be used for vascular access.

The tissue penetrating subassembly 260 may be made of a magnetizable metal including stainless steel needle.

In one or more embodiments, the device 210 may have a standard catheter hub or a blood control hub to connect a catheter 261 to the tissue penetrating subassembly 260. In one or more embodiments, glue, press fitting or another bonding mechanism, such as solvent bonding, is used to secure the catheter 261 to the catheter adapter 267. Standard catheter tubing or custom catheter tubing may be utilized.

In some embodiments, the hub 270 or catheter adapter 267 may be formed from a thermoplastic material, such as polyvinyl chloride, polyethylene, polycarbonate or polyurethane material. Catheter 261 generally comprises an intravenous catheter which includes a biocompatible material, such as a polymer or metallic material. In some embodiments, catheter 261 comprises a flexible polymer material, such as silicon rubber, latex, and/or various thermoplastic elastomers. Catheter 261 may further comprise a rigid polymer or metallic material, as may be desirable for an intended use.

The length and diameter of catheter 261 is generally determined by the application or use for which the intravenous catheter device is intended. Accordingly, one having skill in the art will appreciate that catheter may be modified or adjusted to include any size and dimensions as may be desired or necessary to facilitate a desired use.

In some embodiments, hub 270 comprises an aperture configured to house introducer needle 264 and the proximal end 262 of catheter 261. Introducer needle 264 and the proximal end 262 of catheter 261are fixedly secured to hub 270 such that the introducer needle, intravenous tubing, and catheter adapter 267 form a unitary structure. A fluid pathway or hollow body of introducer needle 264 may be in fluid communication with a fluid pathway of catheter 261.

In one or more embodiments, a catheter adapter 267 may be provided having a proximal end, a distal end and a pathway extending therebetween. A catheter 261 may then be coupled to the distal end of the of a catheter adapter 267, wherein the catheter 261 includes a lumen and a tip. Hub 270 is further provided for supporting introducer needle 264. The introducer needle 264 generally includes a sharpened end, a base, and a hollow body extending therebetween. The base of the introducer needle is coupled to, and supported by the needle adapter. A section of intravenous tubing is further coupled to the needle adapter, wherein the needle adapter facilitates fluid communication between the hollow body of the introducer needle and a fluid pathway of the catheter. The introducer needle, needle adapter, and catheter are then slidably housed within the lumen of the catheter hub adapter.

In one or more embodiments, housing 220 includes a controller 290 in communication with the power supply 240 and the magnetic field generator 230 to control magnitude of the magnetic field generated by the magnetic field generator 230. The controller 290 may include one or more printed circuit boards. The magnetic field generated may be constant or variable.

In one or more embodiments, the power supply 240 may be a plurality of batteries or an AC/DC cord attached to the proximal end of the housing.

In one or more embodiments, hub 270 is detachably connected to the distal end 222 of the housing 220 by a latch 300, which is engaged and disengaged by latch button 310.

In one or more embodiments, the device may include one or more vasculature entry confirmation mechanisms which can be varied in any suitable manner. In one or more embodiments, as shown in FIG. 4, a flash chamber 320 is located within the disposable portion of the tissue penetrating subassembly 260 to visually confirm that blood is flowing through the tissue penetrating subassembly 260 during insertion and to ascertain that the catheter 261 is in the patient' s vein. In one or more embodiments, the introducer needle 264 may have a flashback feature to visualize flashback along the introducer needle before it is directly visible in the flash chamber 320. In one or more embodiments, a notch 340 is located on the distal end of the introducer needle provides immediate confirmation of vessel entry at the point of insertion to improve first-stick success. Catheter 261 may include a notch through which blood can exit the inner lumen to provide flashback confirmation. For example, when using the device, medical personnel can visualize entry of the introducer needle tip into a target anatomical structure, such as a blood vessel. As blood begins to flow along the introducer needle, such as between an introducer needle and a catheter, the medical personnel can see the flashback as the blood enter into the flashback feature. In some embodiments, the flashback confirmation chamber comprises a flashback compartment that is configured to receive blood from the patient's vasculature and to allow the operator to visualize the blood.

Flash chamber 320 and notch 340 may be used with any suitable tissue penetrating device or system including any suitable catheter assembly. By way of illustration, FIG. 4 shows that in a representative embodiment, the flash chamber 320 and notch 340 may be used with a catheter assembly comprising a catheter adapter and a catheter.

In some embodiments, at least a portion of the flashback compartment comprises a translucent or a transparent material that allows the operator to watch the chamber progressively fill with blood. The flashback confirmation chamber may comprise any component that allows (1) the operator to visualize blood filling the confirmation chamber once the cannula of the vascular access device punctures the patient's vasculature, (2) allows the operator to visualize a decrease (i.e., a cessation) of blood flow into the chamber if the distal tip of the cannula is pushed completely through the patient's blood vessel or the blood vessel is transfixed, and (3) allows the chamber to prolong the period of time in which the operator can observe active arterial flashback confirmation from the vascular access device.

The flashback compartment may be any shape that allows it to fulfill its intended purposes. For instance, the flashback compartment may be cylindrical, cuboidal, elongated cuboidal, elliptical, spherical, conical, spiral, irregular, tubular, polygonyl, conical, and/or any other suitable shape. By way of illustration, FIG. 4 shows a representative embodiment in which the flashback compartment is cylindrical.

The confirmation chamber also comprises a vent. The vent can perform any suitable function, including allowing air to exit the flashback compartment as blood enters the catheter, extension tube, and/or flashback compartment. The vent, which is depicted in FIG. 4, may be disposed in any suitable location. By way of example, FIG. 4 shows the vent can be disposed at the proximal end of the flash chamber. The vent may also comprise any component or characteristic that allows it to fulfill its intended purpose.

In one or more embodiments, a flash chamber may be located within the needle hub of the introducer needle. The flash chamber may include a vent plug 330 which seals upon flow of blood into the flashback chamber.

Figure 7:
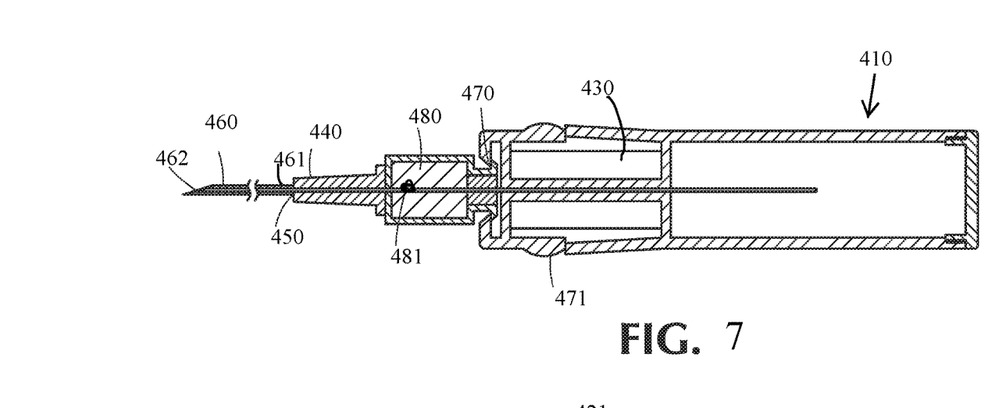
FIG. 7 shows a perspective view of yet another embodiment of a device for magnetizing a tissue-penetrating medical device of the present disclosure including a permanent magnet.

A third aspect of the disclosure pertains to a device for magnetizing a tissue-penetrating medical device having a housing having one or more permanent magnets to which the needle tip is exposed and magnetized. In one or more embodiments, as shown in FIG. 7, the device 410 comprises a housing 420 having a proximal portion 421 and a distal portion 422, one or more permanent magnets 430 contained within the distal portion 422 of housing 420 to produce a magnetic field, and a tissue penetrating subassembly 440 including a hub 450 and a tissue penetrating medical device 460 having a proximal end 461 and a distal end 462, the hub 450 is detachably connected to the distal portion 422 of the housing 420 and the proximal end 461 of tissue penetrating medical device 460 extending proximally from the hub 450 such that the proximal end 461 of the tissue penetrating medical device is exposed to the magnetic field produced by one or more permanent magnets 430 contained within the distal portion 422 of housing 420 and the distal end 462 of the tissue penetrating medical device 460 is magnetized upon exposure of the proximal end 461 of the tissue penetrating medical device 460 by the magnetic field. In one or more embodiments the tissue penetrating medical device 460 is a needle, guidewire or stylet. As described above, the needle can be any type of needle, and in specific embodiments, the needle includes a hollow cannula which can be used for withdrawal or delivery of fluids to a patient.

Figures 8, 9:
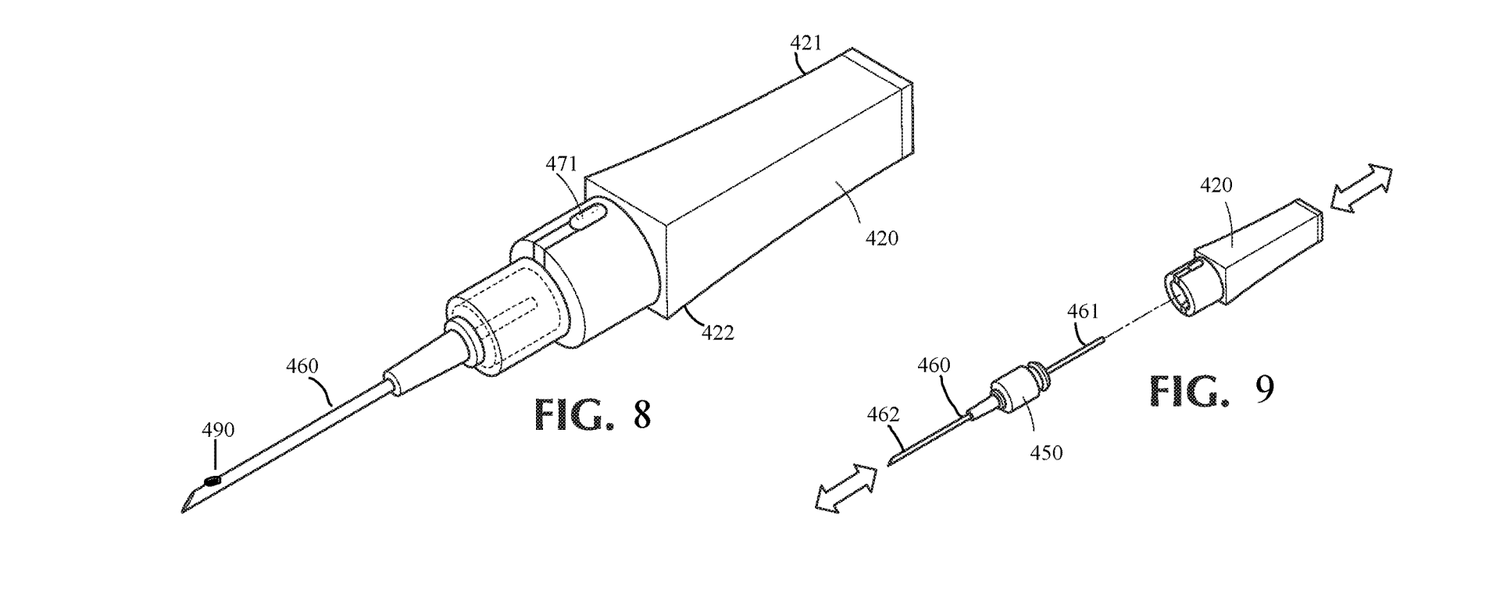
FIG. 8 shows a cross-sectional view of the embodiment as shown in FIG. 7 of a device for magnetizing a tissue-penetrating medical device of the present disclosure.
FIG. 9 shows a perspective view of the embodiment as shown in FIG. 7 of a device for magnetizing a tissue-penetrating medical device of the present disclosure wherein the housing is separated from the tissue penetrating subassembly.

In a specific embodiment, as shown in FIG. 8, the tissue penetrating medical device is a needle, which when magnetized can be used with a procedural guidance system to locate and project the position of the needle during an invasive medical procedure.

In one or more embodiments, as shown in FIG. 9, the hub 450 is detachably connected to the distal portion 422 of the housing 420 by a latch 470 operated by a latch button 471.

In one or more embodiments, as shown in FIG. 7, a flash chamber 480 may located within the hub 450 of the tissue penetrating subassembly 440. In one or more embodiments, the flash chamber includes a vent plug 481 which seals upon flow of blood into the flashback chamber.

In one or more embodiments, as shown in FIG. 8, the tissue penetrating medical device 460 includes a notch 490 to provide immediate confirmation of vessel entry at a point of insertion.

A fourth aspect of the disclosure pertains to a method for magnetizing a tissue-penetrating medical device comprising obtaining a tissue penetrating medical device having an elongated needle having a proximal end and a distal end, the elongated needle disposed in a needle hub subassembly such that the proximal end of the elongated needle extends in a proximal direction from the hub and the distal end of the elongated needle extends in a distal direction from the hub towards a patient. The method includes a user obtaining a housing having a proximal portion and a distal portion wherein the housing includes a magnetic field generator contained within the distal portion of the housing, a power supply in electrical communication with the magnetic field generator, and a switch in communication with the power supply to activate and deactivate the magnetic field generator. The user then connects the needle hub assembly to a distal portion of the housing such that the proximal end of the elongated needle is exposed to the magnetic field generated by the magnetic field generator. The switch in communication with a power supply is depressed to activate a magnetic field generator to magnetize the elongated needle. The user positions the distal end of the elongated needle adjacent to a desired point of vascular entry and the magnetized elongated needle is inserted into a patient's vasculature. In one or more embodiments, the method further includes using an ultrasound imaging device to visualize the magnetized elongated needle.

In practice, a user may use the distal point of the cannula to puncture the skin of a patient and force an over-the-needle peripheral IV catheter into a blood vessel. Once the needle has penetrated the blood vessel and blood flows into the cannula's lumen, a constant or variable magnetic field is produced.

The user attaches the tissue penetrating device to the base of the housing by pressing the tissue penetrating device down onto the base of the housing and snapping it in place.

In this process, the latch resiliently deflects to allow the latch to pass over the catch. Subsequently, the latch returns to its un-deformed positions to prevent displacement of the tissue penetrating device from the housing.

After insertion of the needle/catheter into the patient's vein, the user can detach the needle hub from the housing by pressing the latch button. Once the latch has been disengaged from the slot, the hub having the tissue penetrating device may be removed from the housing, at which time the needle stick protection mechanism will activate. In addition, the introducer needle may also be retracted from the catheter. After use, the cannula may be extracted from the catheter hub, and the needle and cannula may be discarded.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A device comprising:
   a housing having a proximal portion and a distal portion;
   a magnetic field generator contained within the distal portion of the housing to produce a magnetic field, the magnetic field generator includes a coil electrically energized by the magnetic field generator to produce a magnetic field;
   a tissue penetrating subassembly including a hub and a tissue penetrating medical device having a proximal end and a distal end;
   a controller being disposed in the housing and in communication with the magnetic field generator, the controller having a printed circuit assembly that supplies and regulates power to the coil to generate a constant or variable magnetic field around the proximal end of the tissue penetrating medical device; and
   the hub detachably connected to the distal portion of the housing and the proximal end of tissue penetrating medical device extending proximally from the hub such that the proximal end of the tissue penetrating medical device is exposed to the magnetic field and the distal end of the tissue penetrating medical device is magnetized upon exposure of the proximal end of the tissue penetrating medical device by the magnetic field.

2. The device of claim 1, further comprising:
   a power supply in electrical communication with the magnetic field generator; and
   a switch in communication with the power supply to activate and deactivate the magnetic field generator.

3. The device of claim 2, the controller being in communication with the power supply and the magnetic field generator to control magnitude of the magnetic field generated by the magnetic field generator.

4. The device of claim 2, wherein the power supply comprises a direct current power supply.

5. The device of claim 4, wherein the direct current power supply comprises a battery.

6. The device of claim 2, wherein the power supply comprises an alternating current power supply.

7. The device of claim 1, wherein the magnetic field generator is capable of generating a constant magnetic field.

8. The device of claim 1, wherein the magnetic field generator is capable of generating a variable magnetic field.

9. The device of claim 1, wherein the magnetic field generator comprises a permanent magnet.

10. The device of claim 1, wherein the hub is detachably connected to the distal portion of the housing by a latch assembly.

11. The device of claim 1, wherein the tissue penetrating medical device is a needle or stylet.

12. The device of claim 1, wherein the tissue penetrating medical device is a needle and the device further comprises a flash chamber located within the hub of the tissue penetrating medical device.

13. The device of claim 12, wherein the flash chamber includes a vent plug which seals upon flow of blood into the flash chamber.

14. The device of claim 1, wherein tissue penetrating medical device includes a needle having a notch on a distal portion of the needle to provide immediate confirmation of vessel entry at a point of insertion.

15. The device of claim 1, wherein the tissue penetrating medical device is a needle, which when magnetized, can be visualized using an ultrasound imaging device to locate and project a position of the needle during an invasive medical procedure.

16. A device comprising:
   a housing having a proximal portion and a distal portion;
   a magnetic field generator contained within the distal portion of the housing;
   a tissue penetrating subassembly including a catheter having a proximal end and a distal end; an introducer needle extending through the catheter; a catheter adapter having a distal end and a proximal end, an internal cavity, and a tip region having a distal opening having a circumference through which the catheter extends, the catheter adapter being connected to the proximal end of the catheter;
   a controller being disposed in the housing and in communication with the magnetic field generator, the controller having a printed circuit assembly that supplies and regulates power to the magnetic field generator to generate a constant or variable magnetic field around the tissue penetrating medical device; and
   a hub connected to the proximal end of the introducer needle, the hub detachably connected to the distal portion of the housing; the proximal end of the introducer needle extending proximally from the hub such that the proximal end of the introducer needle is exposed to the magnetic field generator and the distal end of the introducer needle is magnetized upon exposure of the proximal end of the introducer needle to the magnetic field generator.

17. The device of claim 16, further comprising:
   a power supply in electrical communication with the magnetic field generator; and a switch in communication with the power supply to activate and deactivate the magnetic field generator.

18. The device of claim 17, the housing further including a controller in communication with the power supply and the magnetic field generator to control magnitude of the magnetic field generated by the magnetic field generator.

19. The device of claim 18, wherein the magnetic field generator is capable of generating a constant magnetic field.

20. The device of claim 18, wherein the magnetic field generator is capable of generating a variable magnetic field.

21. The device of claim 17, wherein the power supply comprises a direct current power supply.

22. The device of claim 21, wherein the direct current power supply comprises a battery.

23. The device of claim 17, wherein the power supply comprises an alternating current power supply.

24. The device of claim 16, wherein the hub is detachably connected to the distal portion of the housing by a latch.

25. The device of claim 16, further comprising a flash chamber located within the hub of the tissue penetrating subassembly.

26. The device of claim 25, wherein the flash chamber includes a vent plug which seals upon flow of blood into the flash chamber.

27. The device of claim 16, wherein the tissue penetrating subassembly comprises a needle including a notch to provide immediate confirmation of vessel entry at a point of insertion.

28. A method of magnetizing a tissue-penetrating medical device comprising:
  obtaining a tissue penetrating medical device having an elongated needle having a proximal end and a distal end, the elongated needle disposed in a needle hub subassembly such that the proximal end of the elongated needle extends in a proximal direction from a hub and the distal end of the elongated needle extends in a distal direction from the hub towards a patient,
  obtaining a housing having a proximal portion and a distal portion; the housing including a magnetic field generator contained within the distal portion of the housing, a power supply in electrical communication with the magnetic field generator; a switch in communication with the power supply to activate and deactivate the magnetic field generator; and a controller being disposed in the housing and in communication with the magnetic field generator, the controller having a printed circuit assembly that supplies and regulates power to the magnetic field generator to generate a constant or variable magnetic field around the tissue penetrating medical device;
  connecting the needle hub subassembly to a distal portion of the housing such that the proximal end of the elongated needle is exposed to the magnetic field generator;
  depressing the switch in communication with a power supply to activate a magnetic field generator to produce a magnetized elongated needle;
  positioning the distal end of the elongated needle adjacent to a desired point of vascular entry; and
  inserting the magnetized elongated needle into a patient's vasculature.

29. The method of claim 28, further comprising using an ultrasound imaging device to visualize the magnetized elongated needle.

* * * * *